(12) United States Patent
McKee et al.

(10) Patent No.: US 7,309,774 B2
(45) Date of Patent: Dec. 18, 2007

(54) ANTIPLASMIN CLEAVING ENZYME

(75) Inventors: Patrick A. McKee, Oklahoma City, OK (US); Kyung N. Lee, Oklahoma City, OK (US); Kenneth W. Jackson, Edmond, OK (US); Victoria J. Christiansen, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 227 days.

(21) Appl. No.: 10/774,242

(22) Filed: Feb. 6, 2004

(65) Prior Publication Data

US 2004/0203102 A1    Oct. 14, 2004

Related U.S. Application Data

(60) Provisional application No. 60/445,774, filed on Feb. 7, 2003.

(51) Int. Cl.
*A61K 35/14*    (2006.01)
(52) U.S. Cl. ........................ 530/380; 530/350
(58) Field of Classification Search ............... None
See application file for complete search history.

(56) References Cited

U.S. PATENT DOCUMENTS

| 5,587,299 A | 12/1996 | Rettig et al. |
| 5,965,373 A | 10/1999 | Zimmermann et al. |
| 6,455,677 B1 | 9/2002 | Park et al. |

FOREIGN PATENT DOCUMENTS

| WO | WO 97/34927 | * | 9/1997 |
| WO | WO 97/34927 A | | 9/1997 |
| WO | PCT/US2004/003398 | | 6/2005 |

OTHER PUBLICATIONS

Goldstein et al., "Molecular cloning of seprase: a serine integral membrane protease from human melanoma," Biochimica et Biophysica Acta., Jul. 10, 1997, vol. 1361, No. 1, pp. 11-19.

Chestukhin et al., "Western blot screening for monoclonal antibodies against human separase," Journal of Immunological Methods, Mar. 1, 2003, vol. 274, No. (1-2), pp. 105-113.

Lind et al., "A novel missense mutation in the human plasmin inhibitor (alpha$_2$-antiplasmin) gene associated with a bleeding tendency", British Journal of Haematology, 1999, vol. 107, pp. 317-322.

Koyama et al., "Different NH$_2$-Terminal Form With 12 Additional Residues of $\alpha_2$-plasmin Inhibitor From Human Plasma and Culture Media of HIP G2 Cells", Biochemical and Biophysical Research communications, Apr. 15, 1994, vol. 200, No. 1, pp. 417-422.

Foekens et al., "The Prognostic Value of Polymorphonuclear Leukocyte Elastase in Patients with Primary Breast Cancer", Cancer Research, vol. 63, No. 2 (Jan. 15, 2003) pp. 337-341. (XP-002394318).

Lee et al., "A novel plasma proteinase potentiates $\alpha_2$-antiplasmin inhibition of fibrin digestion", Blood, vol. 103, No. 10 (May 15, 2004) pp. 3783-3788. (XP-002394321).

Lee et al., "Antiplasmin-cleaving enzyme is a soluble form of fibroblast activation protein", Blood, vol. 107, No. 4 (Feb. 15, 2006) pp. 1397-1404. (XP-002394322).

Park et al., "Fibroblast Activation Protein, a Dual Specificity Serine Protease Expressed in Reactive Human Tumor Stromal Fobroblasts", Journal of Biological Chemistry, vol. 274, No. 51 (Dec. 17, 1999) pp. 36505-36512. (XP-002163938).

Urano et al., "The cleavage and inactivation of plasminogen activator inhibitor type 1 and $\alpha$2-antiplasmin by reptilase, a thrombin-like venom enzyme", Blood Coagulation and Fibronolysis 2000, vol. 11, No. 2 (Mar. 2000) pp. 145-153. (XP009071038).

* cited by examiner

*Primary Examiner*—Hope Robinson
(74) *Attorney, Agent, or Firm*—Dunlap, Codding & Rogers, P.C.

(57) ABSTRACT

Human $\alpha_2$-antiplasmin ($\alpha_2$AP) is the major inhibitor of the proteolytic enzyme plasmin that digests fibrin. Two forms of $\alpha_2$AP circulate in human plasma: a 464-residue protein, which we have termed "pro"-form, or $\alpha_2AP_{pro}$, and an N-terminally-shortened 452-residue "activated"-form, or $\alpha_2AP_{act}$. The latter becomes crosslinked to fibrin by activated factor XIII about 5-fold more rapidly than $\alpha_2AP_{pro}$ and makes fibrin resistant to digestion by plasmin. A new human plasma proteinase has been identified herein that cleaves the Pro12-Asn13 bond of $\alpha_2AP_{pro}$ to yield $\alpha_2AP_{act}$. This enzyme is identified herein as Antiplasmin Cleaving Enzyme (APCE).

2 Claims, 4 Drawing Sheets

ANTIPLASMIN CLEAVING ENZYME

CROSS-REFERENCE TO RELATED APPLICATIONS

This application claims the benefit under 35 U.S.C. 119(e) of U.S. Provisional Application Ser. No. 60/445,774, filed Feb. 7, 2003, which is hereby expressly incorporated by reference herein in its entirety.

STATEMENT REGARDING FEDERALLY SPONSORED RESEARCH OR DEVELOPMENT

Some aspects of this invention were made during the course of Grant HL-072995 awarded by the National Institutes of Health and therefore the Government has certain rights in some aspects of this invention.

BACKGROUND

The present invention is related to, but not limited to, enzymes for cleaving $\alpha_2$-antiplasmin, and inhibitors thereof, and to screening methods for identifying such inhibitors and to methods for treating conditions involving fibrin.

Plasmin plays a critical role in fibrin proteolysis and tissue remodeling (1). Among plasmin inhibitors, $\alpha_2$-antiplasmin ($\alpha_2$AP) is the most important (2). The physiological relevance of plasmin inhibition by $\alpha_2$AP to blood clotting and fibrinolytic homeostasis is supported by the following observations: (i) plasma $\alpha_2$AP inactivates circulating free plasmin in about 0.1 second (1), thereby eliminating the potential for a systemic lytic state that could lead to bleeding; (ii) $\alpha_2$AP is crosslinked to forming fibrin by activated blood clotting factor XIII (FXIIIa) and inhibits plasmin-mediated lysis in direct proportion to the amount incorporated (3,4); (iii) patients with homozygous $\alpha_2$AP deficiency manifest serious hemorrhagic tendencies, while heterozygotes tend to hemorrhage only after major trauma or surgery (5); (iv) two adult patients with relatively large patent ducti arteriosi (PDA) were successfully treated by continuous intravenous $\alpha_2$AP to stabilize induced thrombi within the PDA until completely occlusive and ready for fibrous organization (6); and (v), in mice homozygous for targeted $\alpha_2$AP gene disruption ($\alpha_2$AP$^{-/-}$), experimental induction of thrombi took longer, bleeding times were prolonged, and vascular patency was more readily established when compared with wild-type mice (7). The sum of these observations underscores the importance of $\alpha_2$AP on the progression and survival of physiologic and pathologic fibrin formation.

$\alpha_2$-Antiplasmin ($\alpha_2$AP) is therefore a blood plasma protein that rapidly and specifically inhibits the enzyme, plasmin, which digests blood clots, whether presenting early as intravascular platelet-fibrin deposits or as partially or completely occlusive thrombi. Similarly, plasmin and $\alpha_2$AP activities are important to the development and survival of fibrin as occurs in inflammation, wound healing and virtually all forms of cancer and its metastases. Human $\alpha_2$AP is synthesized primarily in the liver and secreted into plasma as a 68-kDa single polypeptide chain having Met as the N-terminus and containing 464 amino acids and 13% carbohydrate (1,8). During circulation in plasma, the secreted precursor Met-$\alpha_2$AP form undergoes proteolytic cleavage between Pro12-Asn13 to yield a truncated version with Asn as the new N-terminus, i.e., Asn-$\alpha_2$AP (8). The latter becomes crosslinked to fibrin about 3-fold faster than recombinant Met-$\alpha_2$AP (9). Despite the likelihood that this observation is physiologically important, an enzyme responsible for this cleavage previously has been unknown.

It was therefore a desirable objective to isolate and identify the plasma enzyme responsible for the cleavage of $\alpha_2$-antiplasmin into the active form.

DESCRIPTION OF THE INVENTION

As noted elsewhere herein, an objective of the present work was to discover the previously unknown enzyme or causative agent for the cleavage of precursor $\alpha_2$-antiplasmin into activated $\alpha_2$-antiplasmin.

Figure 1:
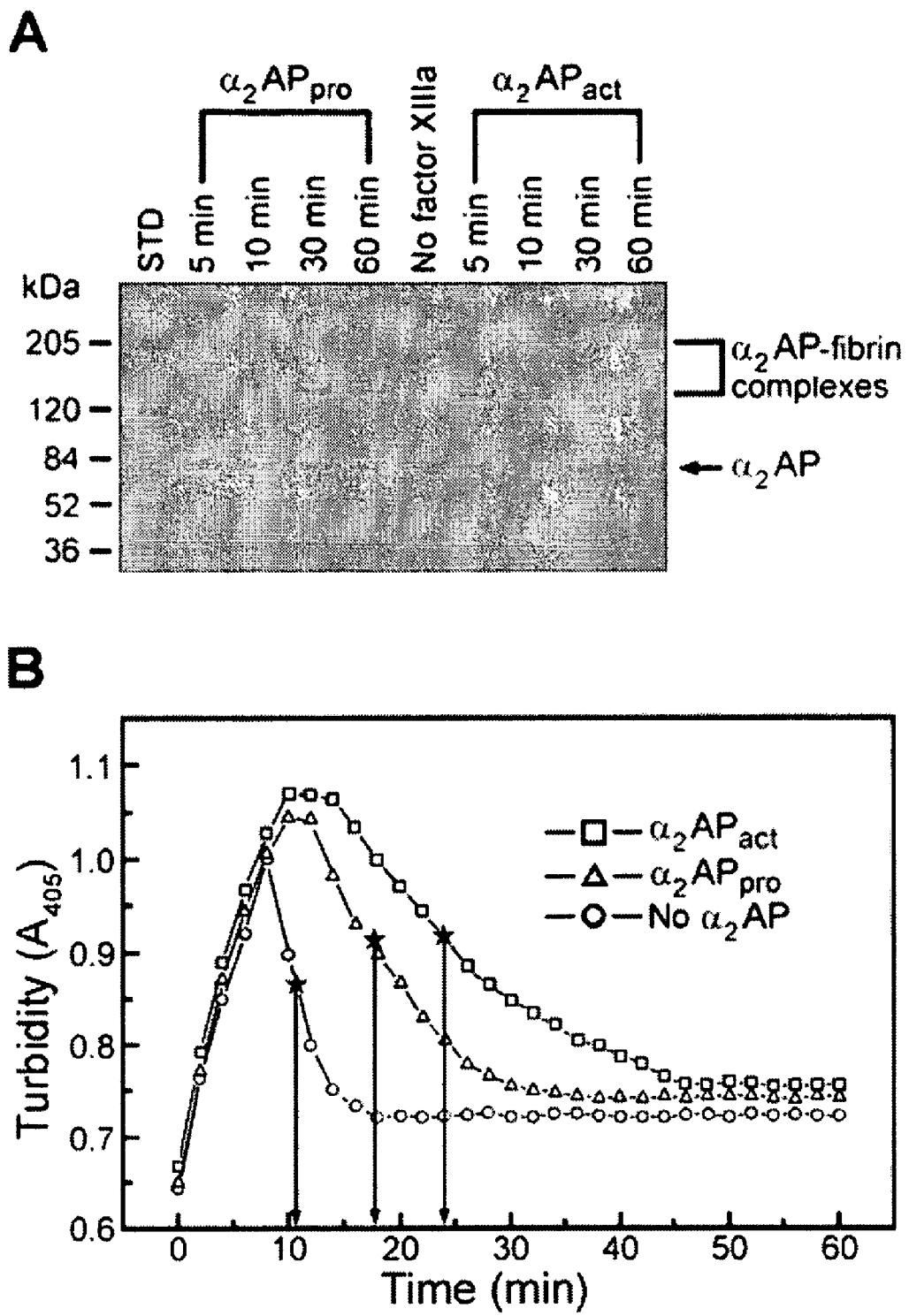
FIG. 1. Human $\alpha_2$AP$_{act}$ is crosslinked to fibrin faster and makes a plasma fibrin clot more resistant to lysis as compared to $\alpha_2$AP$_{pro}$. (A) Time-dependent crosslinking of $\alpha_2$AP$_{pro}$ and $\alpha_2$AP$_{act}$ to fibrin by FXIIIa catalysis. Human $\alpha_2$AP (1 µM), fibrinogen (6 µM), and FXIII (50 nM) were clotted with thrombin (5 units/ml) and CaCl$_2$(10 mM). After incubation at 37° C. for selected time intervals, the clots were solubilized in 9 M urea-3% SDS-10 mg/ml DTT and subjected to SDS-PAGE. Proteins were transferred to a nitrocellulose membrane, and detected using a monoclonal antibody to the C-terminal region of $\alpha_2$AP and horseradish peroxidase labeling. (B) UK-induced plasma clot lysis patterns in the presence of $\alpha_2$AP$_{act}$ (□), $\alpha_2$AP$_{pro}$ (Δ) or $\alpha_2$AP-depleted plasma only (○). After adding $\alpha_2$AP$_{pro}$ or $\alpha_2$AP$_{act}$ (0.42 µM) to $\alpha_2$AP-depleted plasma, instant fibrin clot formation and initiation of fibrinolysis was achieved by adding a mixture of thrombin, CaCl$_2$, and UK to give final concentrations of 1 unit/ml, 16 mM, and 45 units/ml, respectively. Turbidity change was monitored as absorbance at 405 nm. PCLTs were defined as midpoint times (★).

We isolated native forms of both Met-$\alpha_2$AP and Asn-$\alpha_2$AP from human plasma, and studied these instead of recombinant forms. A purified mixture of Met-$\alpha_2$AP and Asn-$\alpha_2$AP was isolated from human plasma (2) and then Met-$\alpha_2$AP was isolated from the mixture on an immunoaffinity column with goat antibody specific for the N-terminal 12-amino acid peptide of Met-$\alpha_2$AP. Based on differences in crosslinking rates, we refer to Met-$\alpha_2$AP as or the precursor form of $\alpha_2$AP "pro"-$\alpha_2$AP ($\alpha_2$AP$_{pro}$), and its derivative, Asn-$\alpha_2$AP, as "activated"-$\alpha_2$AP ($\alpha_2$AP$_{act}$). To analyze crosslinking rates, mixtures of fibrinogen, $Ca^{2+}$, FXIII, and $\alpha_2$AP$_{pro}$ or $\alpha_2$AP$_{act}$ were clotted by thrombin and analyzed by Western blots of reduced SDS-PAGE gels. FIG. 1A shows that $\alpha_2$AP immunoreactivity increases with time in high molecular weight crosslinked complexes of $\alpha_2$AP-fibrin; simultaneously immunoreactivity decreases in the lower molecular weight $\alpha_2$AP band. $\alpha_2$AP$_{act}$ crosslinked to fibrin more than 5-fold faster than $\alpha_2$AP$_{pro}$ as determined by comparisons of band intensities. In contrast, both native $\alpha_2$AP$_{pro}$ and $\alpha_2$AP$_{act}$ inhibited proteolytic activity at the same rate when incubated in solution with an equimolar amount of plasmin.

To evaluate if $\alpha_2$AP$_{act}$ protects fibrin from fibrinolysis more effectively than $\alpha_2$AP$_{pro}$, the two forms were compared by urokinase (UK)-induced plasma clot lysis. After addition of $\alpha_2$AP$_{pro}$ or $\alpha_2$AP$_{act}$ to $\alpha_2$AP-depleted plasma, a mixture of thrombin, $Ca^{2+}$, and UK was added to catalyze crosslinked fibrin formation and to initiate fibrinolysis, according to a method (4) previously described. As shown in FIG. 1B, turbidity was monitored as absorbance at 405 nm and plasma clot lysis times (PCLTs) were defined as the midpoint between the highest absorbance and constant lowest absorbance. A control clot prepared from $\alpha_2$AP-depleted plasma gave a PCLT of 10.5 min. With addition of $\alpha_2$AP$_{pro}$ or $\alpha_2$AP$_{act}$, PCLTs were 17.5 and 24.0 min, respectively, demonstrating that fibrinolysis was inhibited to a lesser extent by $\alpha_2$AP$_{pro}$ than by $\alpha_2$AP$_{act}$.

The effects of $\alpha_2$AP$_{pro}$ and $\alpha_2$AP$_{act}$ were also compared by fibrin clot lysis times (FCLTs) using a purified system containing $\alpha_2$AP, fibrinogen, plasminogen, thrombin, $Ca^{2+}$, and UK as previously described (10). In the presence of $\alpha_2$AP$_{act}$, FCLT was increased by 42% over $\alpha_2$AP$_{pro}$, which is comparable to the 37% increase observed for the PCLT. Hence removal of the N-terminal 12-residue peptide from $\alpha_2$AP$_{pro}$ by a proteinase yields the derivative $\alpha_2$AP$_{act}$ that is more efficiently crosslinked to fibrin and as a consequence, inhibits fibrinolysis more effectively.

Figure 2:
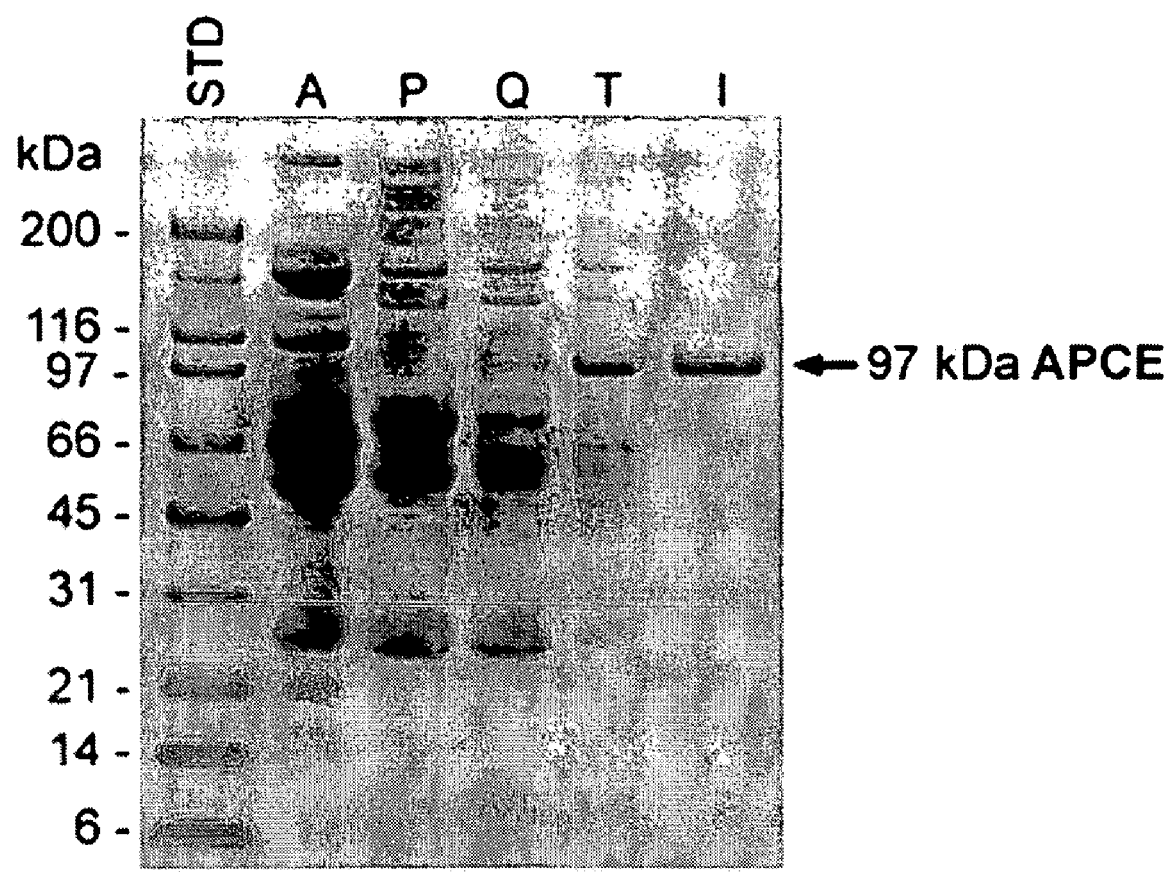
FIG. 2. Purification of APCE. Coomassie blue-stained gel of protein sample obtained from each purification step. Proteins were analyzed on a 10%-20% gradient SDS-PAGE under reducing conditions. STD, molecular-weight standards with molecular weights shown in kDa on the left; A, ammonium sulfate fraction (15-40%); P, phenyl-Toyopearl chromatography fraction; Q, Q-sepharose chromatography fraction; T, T-gel thiophilic chromatography fraction; I, immunoaffinity chromatography fraction.

Given the greater efficiency of $\alpha_2$AP$_{act}$ incorporation into fibrin, we reasoned that the unidentified agent responsible for converting $\alpha_2$AP$_{pro}$ to $\alpha_2$AP$_{act}$ might be important in modulating the susceptibility of fibrin to plasmin and therefore undertook its isolation. As shown in FIG. 2, a proteinase was purified from human plasma using an initial ammonium sulfate fractionation (A), followed by the sequence of phenyl hydrophobic interaction (P), Q-sepharose anion exchange (Q), T-gel thiophilic (T), and immunoaffinity (I) chromatography steps. The agent was isolated from fresh-frozen human plasma by sequential steps that began with ammonium sulfate precipitation, with Z-Gly-Pro-pNA-hydrolyzing activity identified in the 15-40% fraction. The pellet was dissolved in 10% ammonium sulfate and then applied to a phenyl-hydrophobic interaction chromatography column and bound proteins were eluted by a decreasing ammonium sulfate gradient (5-0%). Active fractions were pooled and further purified by an increasing NaCl gradient (0-0.5 M) elution on a Q-sepharose anion exchange column. Following adsorption and elution from a T-gel thiophilic column, an N-terminal sequence of the dominant protein in the active fractions, as judged by SDS-PAGE, was determined by Edman sequence analysis.

Figure 3:
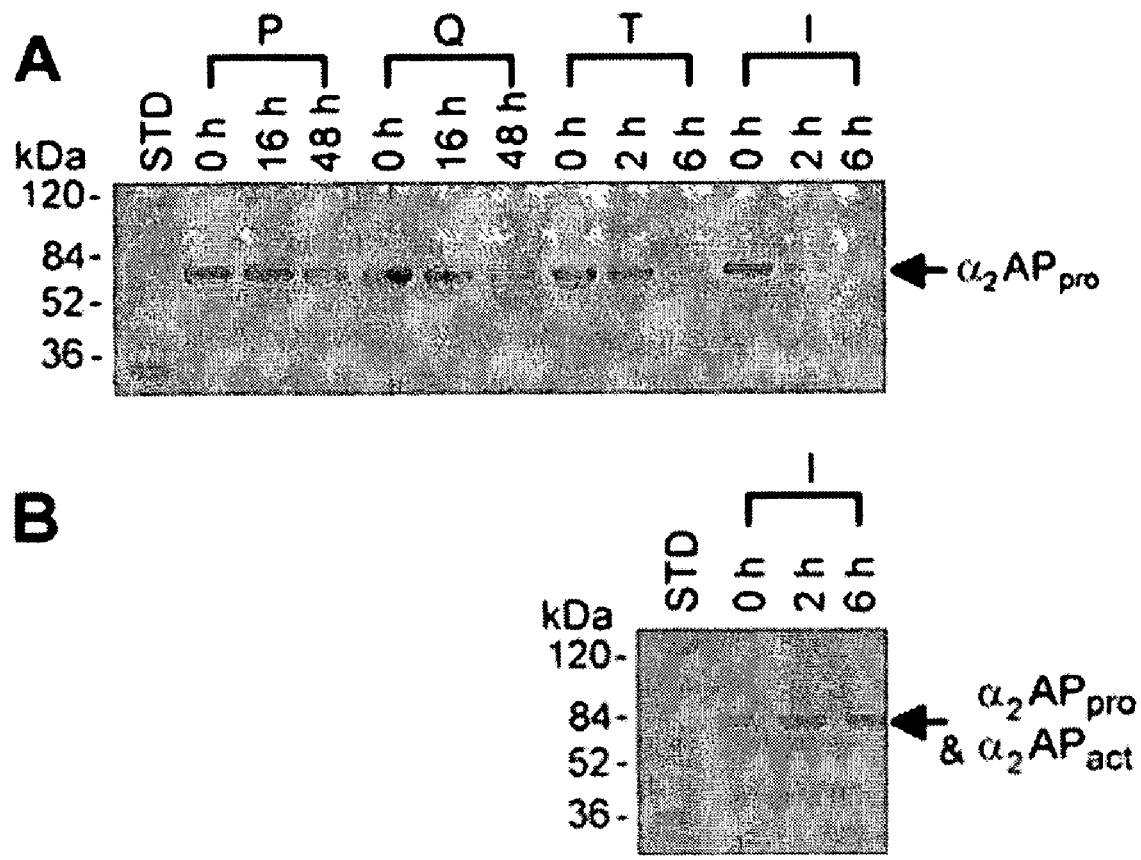
FIG. 3. (A) $\alpha_2$AP$_{pro}$ immunoblot analysis demonstrating that APCE activities increase with each purification step. $\alpha_2$AP$_{pro}$ (5 µg) and each chromatographic sample (54 µg P, 9 µg Q, 0.6 µg T, or 0.2 µg I) were incubated at 22° C. for the times shown, and an aliquot of each reaction mixture was subjected to SDS-PAGE, transferred to a nitrocellulose membrane, and $\alpha_2$AP$_{pro}$ was detected using an antibody specific for its N-terminal peptide and horseradish peroxidase labeling. (B) $\alpha_2$AP immunoblot analysis demonstrating that incubation of $\alpha_2$AP with the immunoaffinity chromatography sample does not result in the loss of $\alpha_2$AP band intensity or in the appearance of bands less than 68-kDa. $\alpha_2$AP$_{pro}$ (5 µg) and 0.2 µg of the immunoaffinity chromatography sample (I) were incubated at 22° C. for the times shown, and an aliquot of each reaction mixture was subjected to SDS-PAGE, transferred to a nitrocellulose membrane, and $\alpha_2$AP was detected using a monoclonal antibody reactive to either form.

Based upon the N-terminal sequence obtained, a multiple antigenic peptide (MAP) was prepared for use as an antigen to immunize a goat. The antibody was purified from the goat serum to prepare an immunoaffinity column. The pooled fractions from the T-gel column were then applied to the immunoaffinity column. After washing, the column was eluted with 3 M sodium thiocyanate, pH 7.5 and the eluate sample was buffer-changed into 25 mM sodium phosphate-1 mM EDTA, pH 7.5 by Centricon ultrafiltration. Following SDS-PAGE and electrotransfer of sample T to a PVDF membrane, the N-terminal sequence of a 97-kDa band was determined by Edman sequence analysis. For the immunoaffinity (I) column, we used a purified goat antibody to a synthetic peptide containing the 15 N-terminal residues (IVLRPSRVHNSEENT-SEQ ID NO:1) of the 97-kDa protein band in sample T. During the purification steps, proteolytic activity of the agent was monitored by hydrolysis of Z-Gly-Pro-pNA (11). Active fractions in each purification step were pooled and analyzed by SDS-PAGE (FIG. 2); cleavage activity towards $\alpha_2$AP$_{pro}$ was assessed by immunoblot analyses (FIG. 3A).

FIG. 2 shows that the intensity of the 97-kDa protein increased at each purification step; and FIG. 3A shows that proteolytic activity towards $\alpha_2$AP$_{pro}$ increased as the purification progressed. When $\alpha_2$AP$_{pro}$ was incubated with protein eluted in the final immunoaffinity purification step I, it was completely and specifically cleaved at the Pro12-Asn13 bond of the $\alpha_2$AP$_{pro}$ as shown by: (i) The 68-kDa band, which had been easily demonstrable at 0 time by antibody specific for $\alpha_2$AP$_{pro}$, completely disappeared by 6 h (FIG. 3A-I). When immunostained with an antibody to $\alpha_2$AP$_{act}$, however, the intensity of the 68-kDa band at 0 h and 6 h did not change (FIG. 3B). Also no bands less than 68-kDa were detected in the 6 h incubation sample. (ii) N-terminal analyses of the 0 h incubation sample showed only the $\alpha_2$AP$_{pro}$ sequence, MEPLGRQLTSGP (SEQ ID NO:2), while the 6 h sample had only the $\alpha_2$AP$_{act}$ N-terminal sequence, NQEQVSPLTLLK (SEQ ID NO:3). The proteinase isolated by the last purification step showed a single 97-kDa band (FIG. 2-I), with an N-terminal sequence identical to that of the major protein band in sample T. Surprisingly, the sequence also matched that deduced from the cDNA sequence for Ile24-Thr38 of fibroblast activation protein (FAP) (12), a proline-specific serine proteinase also termed seprase by another group (13).

To determine additional sequence information from the protein, the 97-kDa protein band from the SDS-PAGE gel was reduced, alkylated, and digested with trypsin (14). The tryptic digest was subjected to liquid chromatography-mass spectrometry-mass spectrometry (LC/MS/MS) to obtain molecular weights and MS/MS fragment ion spectra to utilize the MASCOT MS/MS ion search engine to query the OWL non-identical protein database (15). From our search results, five peptides had sequences in common with FAP/seprase (12,13): residues 210-219 (YALWWSPNGK-SEQ ID NO:4); residues 247-254 (TINIPYPK-SEQ ID NO:5); residues 487-499 (ILEENKELENALK-SEQ ID NO: 6); residues 500-509 (NIQLPKEEIK-SEQ ID NO:7); and residues 522-530 (MILPPQFDR-SEQ ID NO: 8).

This degree of homology suggests that the 97-kDa proteinase, referred to herein as antiplasmin cleaving enzyme (APCE), has similarities to FAP/seprase, but significant differences remain. FAP/seprase is reported to be expressed on the cell surface of reactive stromal fibroblasts of healing wounds and epithelial cancers, but not on normal tissue or benign epithelial tumors (16,17), and is believed to be particularly associated with an invasive phenotype of human melanoma and carcinoma cells (13). Despite the plausibility that FAP/seprase may have a role in tissue remodeling, a physiological substrate has not been demonstrated for the native enzyme, and hence a clearly defined biologic function remains obscure. Although gelatin and collagen I appeared to serve as substrates for recombinant FAP expressed on a human embryonal kidney epithelial cell line (293 cells), products of fragmentation or actual cleavage sites were not identified (18). Neither soluble FAP nor its cleavage products appear to exist in the circulation (19); however, the APCE we describe here was isolated from human plasma.

Therefore, without wishing to be bound by theory, it is possible that human plasma APCE is a proteolytically-derived form of the cell membrane-bound FAP/seprase. This possibility is raised by the following observations: (i) the N-terminal sequence of APCE starts with Ile, which corresponds to the $24^{th}$ residue of FAP/seprase, the latter estimated to have its first six N-terminal amino acids in the fibroblast cytoplasm, with another predicted 20-residue transmembrane domain, and then a 734-residue extracellular C-terminal catalytic domain (12,13); (ii) internal sequences of APCE obtained from five tryptic peptides over a fairly long segment (residues 210 through 530) are identical to that deduced from cDNA sequence of FAP/seprase; (iii) non-denaturing gel filtration chromatography of APCE is consistent with a native mass in a dimeric form of about 180 kDa, and whether or not reduced, its denatured (monomeric) molecular weight by SDS-PAGE is about 97 kDa (FIG. 2-I), both values are consistent with the reported dimeric structure of 190 kDa for FAP/seprase (18); and (iv) APCE is inhibited by DFP, PMSF, and AEBSF, but not by iodoacetate, E-64, or EDTA, just as reported for FAP/seprase (18); (v) analogously, a closely related type II transmembrane protease is postulated to undergo proteolytic cleavage of its N-terminal 38-residue cytoplasmic/transmembrane domain to give rise to the circulating human dipeptidyl peptidase IV (DPP IV, aka T-cell activation CD26, with 50% homology to FAP/seprase) (20); however, DPP IV cleaves only N-terminal dipeptides from polypeptides with proline or alanine at the penultimate position (11) and does not cleave Pro12-Asn13 of $\alpha_2AP_{pro}$ as does APCE.

If APCE indeed results from proteolysis of the transmembrane domain of FAP/seprase, a proteinase that might cleave the Cys23-Ile24 bond has yet to be identified. The hydrophobic residue Ile24 as the $P_1'$ position of the bond could make this a preferred cleavage site for an extracellular enzyme such as a matrix metalloproteinase (21). Alternatively, APCE may be a product of intracellular processing. Conceivably, two pathways exist in the same cell: one which normally synthesizes, processes and secretes APCE without a transmembrane segment; and another which produces a membrane-bound enzyme, i.e., FAP/seprase when fibroblasts become activated and proliferate in inflammatory states, embryogenesis, or metastases of certain epithelial-derived malignancies (16,17). Finally, the possibility remains that APCE is a product of a different gene, or that it results from alternative splicing. Our data indicate that APCE is produced under normal physiological states, and unlike the case with FAP/seprase, pathological disorders are not required to stimulate gene expression. The fact that APCE is found in normal plasma and cleaves $\alpha_2AP_{pro}$ suggests that one of its physiologic functions is the regulation of $\alpha_2AP_{act}$ availability for plasmin inhibition within crosslinked fibrin.

We investigated whether APCE is present in animal plasmas other than human. Recently phenyl hydrophobic interaction chromatography was used to separate two distinct Z-Gly-Pro-AMC-hydrolyzing activities from bovine serum; one bound to the phenyl column, while the other did not (22). We obtained a similar result when ammonium sulfate-fractionated human plasma was subjected to phenyl-column chromatography. But only the bound activity cleaved $\alpha_2AP_{pro}$ (FIG. 3A-P). Since fetal bovine serum in cell culture media was reported to contain an enzyme activity that cleaves the Pro12-Asn13 bond of human $\alpha_2AP_{pro}$ (8), it might be speculated that the phenyl-bound fraction from bovine serum experiments (22) possessed $\alpha_2AP_{pro}$-cleaving activity; however, the protein was not tested in this regard and not sufficiently characterized to allow comparison to APCE.

The fact that the N-terminal sequence of bovine $\alpha_2AP$ (23) has no homology to human $\alpha_2AP$, and lacks a Pro-Asn bond in its N-terminal region (Table 1), prompted us to assay APCE activities and N-terminal sequences of $\alpha_2AP$ from selected animal species to assess if APCE-mediated cleavage of $\alpha_2AP_{pro}$ is a general phenomenon. To screen APCE activity in other animal plasmas, Z-Gly-Pro-AMC and Z-Gly-Pro-pNA were avoided, since more than one enzyme cleaves these substrates in human and bovine plasma and serum, and the same might hold for other species. Although we developed an assay (FIG. 3) to show that $\alpha_2AP_{pro}$ is a substrate for APCE, the assay is not convenient for screening purposes. Therefore to measure APCE activity in human and other animal plasma with greater specificity than provided by Z-Gly-Pro-pNA and greater sensitivity than $\alpha_2AP_{pro}$, we designed a fluorescent resonance energy transfer (FRET) peptide substrate that contained the APCE-sensitive Pro12-Asn13 bond within the Thr9-Gln16 sequence of $\alpha_2AP_{pro}$.

The FRET peptide comprised Arg-Lys(DABCYL)-Thr-Ser-Gly-Pro-Asn-Gln-Glu-Gln-Glu(EDANS)-Arg (SEQ ID NO:9). Hydrolysis of the Pro-Asn bond separates the fluorophore, EDANS {5-[(2-aminoethyl)amino]-naphthalene-1-sulfonic acid} from the quenching group, DABCYL {4-(4-dimethylaminophenylazo)benzoyl} to give an increase in fluorescence. APCE cleavage of the Pro-Asn bond in the FRET peptide substrate was confirmed by analysis of products by LC/MS. In contrast to APCE assay results where Z-Gly-Pro-pNA was used, only the phenyl-bound fraction possessed the ability to cleave the FRET peptide substrate. It is important to note that DPP IV did not cleave the FRET peptide or $\alpha_2AP_{pro}$. Hence, the FRET peptide and $\alpha_2AP_{pro}$ appear to be specific substrates for APCE. $\alpha_2$-antiplasmin cleaving enzyme preferably has a specific activity of at least $52644 \times 10^{-3}$ fluorescence intensity (FI) units per milligram, wherein FI is defined as total fluorescence intensity produced by APCE-catalyzed FRET peptide cleavage during a 2-hour incubation at 22° C.

TABLE 1

| Sample | APCE activity[a] | $\alpha_2AP_{act}/\alpha_2AP_{pro}$ ratio[b] | N-terminal sequence(s) of $\alpha_2$AP | | | | | SEQ ID NO. |
|---|---|---|---|---|---|---|---|---|
| | | | 1 | 5 | 10 | 15 | 20 | |
| Human | 606 | 2.70 | MEPLG | RQLTS | GPNQE | QVSP L | | 12 |
| | | | NQEQV | S PLT L | LKLGN | QEPGG | | 13 |
| Chimpanzee | 653 | 2.31 | MEPLG | RQLTS | GPNQE | QVSP | | 14 |
| | | | NQEQV | S PLT L | LKLGN | QEPG | | 15 |
| Baboon | 601 | 0.25 | MEPLG | WQLTS | GPNQE | RVP PL | | 16 |
| | | | NQERV | P PLT L | LKLGN | QEPGG | | 17 |
| Bovine | 560 | Single form | F SPVS | TMEPL | DLQLM | DGQAQ[c] | | 18 |
| Murine | 662 | Single form | VDLPG | QQPVS | EQAQQ | K LPL P[c] | | 19 |
| Ostrich | 652 | Single form | LQVDY | L VLEV | A[c] | | | 20 |

Table 1. Comparison of APCE activity, $\alpha_2AP_{act}/\alpha_2AP_{pro}$ ratio, and $\alpha_2$AP N-terminal sequence in human plasma with those in animal plasma.
[a] RK(DABCYL)-TSGPNQEQE(EDANS)R substrate (SEQ ID NO:9) (100 μM, 10 μl) was added to 40 ml of plasma diluted with 150 μl of 50 mM Tris-150 mM NaCl-1 mM EDTA, pH 7.5, and incubated at 22° C. The increase of fluorescence intensity was monitored with time at excitation and emission wavelengths of 360 and 460 nm, using a BIO-TEK FL600 fluorescence plate reader. APCE activity was obtained by linear regression analyses of early time points and reported as fluorescence intensity/hour. Plasma samples were prepared from citrated blood of 5 humans, 6 chimpanzees, 5 baboons, 10 cows, 6 mice, or 2 ostriches.
[b] N-terminal sequence analysis of $\alpha_2$AP purified from pooled human, chimpanzee and baboon plasma revealed two sequences. One sequence began with Met($\alpha_2AP_{pro}$); the second sequence started with Asn($\alpha_2AP_{act}$). The ratio of $\alpha_2AP_{act}/\alpha_2AP_{pro}$ was expressed as (pmol of Asn)/(pmol of Met).
[c] Only a single N-terminal sequence was reported for purified $\alpha_2$AP from bovine, murine and ostrich plasma (23-25).

Using the FRET peptide substrate described above, APCE activity was assessed in other selected animal plasmas. As shown in Table 1, plasma APCE activity levels in the different animal species we tested are similar. Interestingly, however, published N-terminal amino acid sequences from bovine (23), murine (24), and ostrich (25) $\alpha_2$AP lack homology to human $\alpha_2$AP and none contain the APCE-susceptible Pro12-Asn13 bond. We then elected to purify and determine N-terminal sequences of $\alpha_2$AP from animals more closely related to human, namely chimpanzee and baboon. In each instance, $\alpha_2$AP was found to circulate as both $\alpha_2AP_{pro}$ and $\alpha_2AP_{act}$ forms and to have an APCE-susceptible Pro12-Asn13 bond in $\alpha_2AP_{pro}$ (Table 1). $\alpha_2AP_{pro}$ purified from separate plasma samples from six unrelated chimpanzees had exactly the same N-terminal sequence as human, except that we noted an Arg6Trp polymorphism for several human $\alpha_2AP_{pro}$ samples, while chimpanzees had Arg6 only. $\alpha_2AP_{pro}$ purified from a pool of five baboon plasma samples was closely similar to that of human, including the Pro12-Asn13, but different amino acids were found in three positions: Trp6, Arg16, and Pro18.

N-terminal sequence data show that ratios of $\alpha_2AP_{act}/\alpha_2AP_{pro}$ were much higher in human (2.70) and chimpanzee (2.31) than in baboon plasma (0.25), despite similar APCE activities (Table 1). These data imply that APCE cleavage of $\alpha_2AP_{pro}$ is not only dependent on $P_1$ and $P_1'$ sites (Pro12-Asn13), but also on extended sites, noting that three residues, Arg6, Gln16, and Ser18 in human and chimpanzee $\alpha_2AP_{pro}$ contrast to the Trp6, Arg16 and Pro18 we found in baboon $\alpha_2AP_{pro}$.

There may be physiologically important substrates for APCE other than $\alpha_2AP_{pro}$, since in contrast to human, chimpanzee and baboon plasmas, some animals have only a single form of $\alpha_2$AP, which lacks any Pro-Asn bond in the N-terminal region (Table 1). Although $\alpha_2$AP would not be a substrate, other substrates for APCE may exist in their plasma or tissue. For example, Z-Gly-Pro-AMC-hydrolyzing activity is suggested to play a role in the degradation of behaviorally active neuropeptides (26). Another group has reported that thyrotropin-releasing hormone is cleaved by phenyl-bound Z-Gly-Pro-AMC-hydrolyzing activity in bovine serum (22).

Our data indicate that human $\alpha_2AP_{pro}$ is a physiologically important substrate of APCE, since proteolytic cleavage between Pro12-Asn13 yields the derivative form $\alpha_2AP_{act}$, which becomes crosslinked significantly faster to fibrin by FXIIIa, and as a consequence, enhances the resistance of fibrin to digestion by plasmin. Since human APCE augments the inhibition of fibrinolysis by increasing the availability of the faster crosslinking form, i.e., $\alpha_2AP_{act}$, potent and selective inhibitors of APCE might allow titration of $\alpha_2AP_{act}$ production to lower in vivo levels, and thereby enhance both endogenous and exogenous fibrin removal. In those clinical situations where fibrin formation is likely, the development of an APCE inhibitor might decrease the amount of $\alpha_2AP_{act}$ available for crosslinking with fibrin as thrombi develop or inflammation progresses, and then endogenous levels of generated plasmin, or plasmin produced by administering small amounts of plasminogen activator, might be sufficient to effect fibrin removal so that vessel patency and organ function are maintained. Low ratios of $\alpha_2AP_{act}/\alpha_2AP_{pro}$ should not greatly enhance risk of plasmin-induced systemic bleeding because: (i) each form would still be available for incorporation into fibrin, albeit mostly at the slower rate of the predominant $\alpha_2AP_{pro}$. Such fibrin should be adequate for hemostasis, but any intravascular fibrin deposits that form under these circumstances will be more vulnerable than usual to removal by modest increases of fibrinolytic activity; and (ii) the circulating plasmin-neutralizing capacity of non-fibrin bound, or free $\alpha_2$AP, should be fairly normal, since both $\alpha_2AP_{act}$ and $\alpha_2AP_{pro}$ inhibit plasmin equally well in a solution environment.

As noted earlier, $\alpha_2$-antiplasmin ($\alpha_2$AP) is a blood plasma protein that rapidly and specifically inhibits the enzyme, plasmin, which digests blood clots, whether presenting early as intravascular platelet-fibrin deposits or as partially or completely occlusive thrombi. Similarly, plasmin and $\alpha_2$AP activities are important to the development and survival of fibrin as occurs in inflammation, wound healing and virtually all forms of cancer and its metastases. We determined that $\alpha_2$AP exists in blood in two forms in the following percentages: (1) the precursive form ($\alpha_2AP_{pro}$), at about 30% of the total $\alpha_2$AP; and (2) its derivative, the "activated" form ($\alpha_2AP_{act}$), produced by cleavage of the Pro12-Asn 13 bond in the N-terminal region of $\alpha_2AP_{pro}$, at about 70% of total circulating $\alpha_2AP$. Our experiments show that $\alpha_2AP_{act}$ is incorporated into forming fibrin about 5 times faster than $\alpha_2AP_{pro}$. More recent data produced by us indicate that $\alpha_2AP_{pro}$ has an Arg6Trp polymorphism, shown by us to be due to a single nucleotide polymorphism (SNP). The Arg6-form of $\alpha_2AP_{pro}$ is cleaved by APCE about 8-fold faster than Trp6-form of $\alpha_2AP_{pro}$. This observation fits with our findings that $\alpha_2AP_{act}/\alpha_2AP_{pro}$ ratios are significantly higher in human plasma containing $\alpha_2AP_{pro}$(Arg6), than in plasma containing $AP_{pro}$(Trp6).

The more $\alpha_2AP_{act}$ available for incorporation into forming fibrin during the initial stages of atherosclerotic plaque formation, usually consisting of platelet-fibrin deposition, or during occlusive thrombi development to cause strokes, and heart attacks, the more resistant these lesions become to removal by endogenous or exogenous generated plasmin. Persons with the Arg6 genotype, i.e., homozygous, may be more vulnerable to atherosclerosis and its thrombotic complications, or to other diseases as a consequence of $\alpha_2AP$/fibrin/plasmin mechanisms, and hence determining a patient's genotype with respect to the SNP would be useful in designing preventive and therapeutic strategies.

Figure 4:
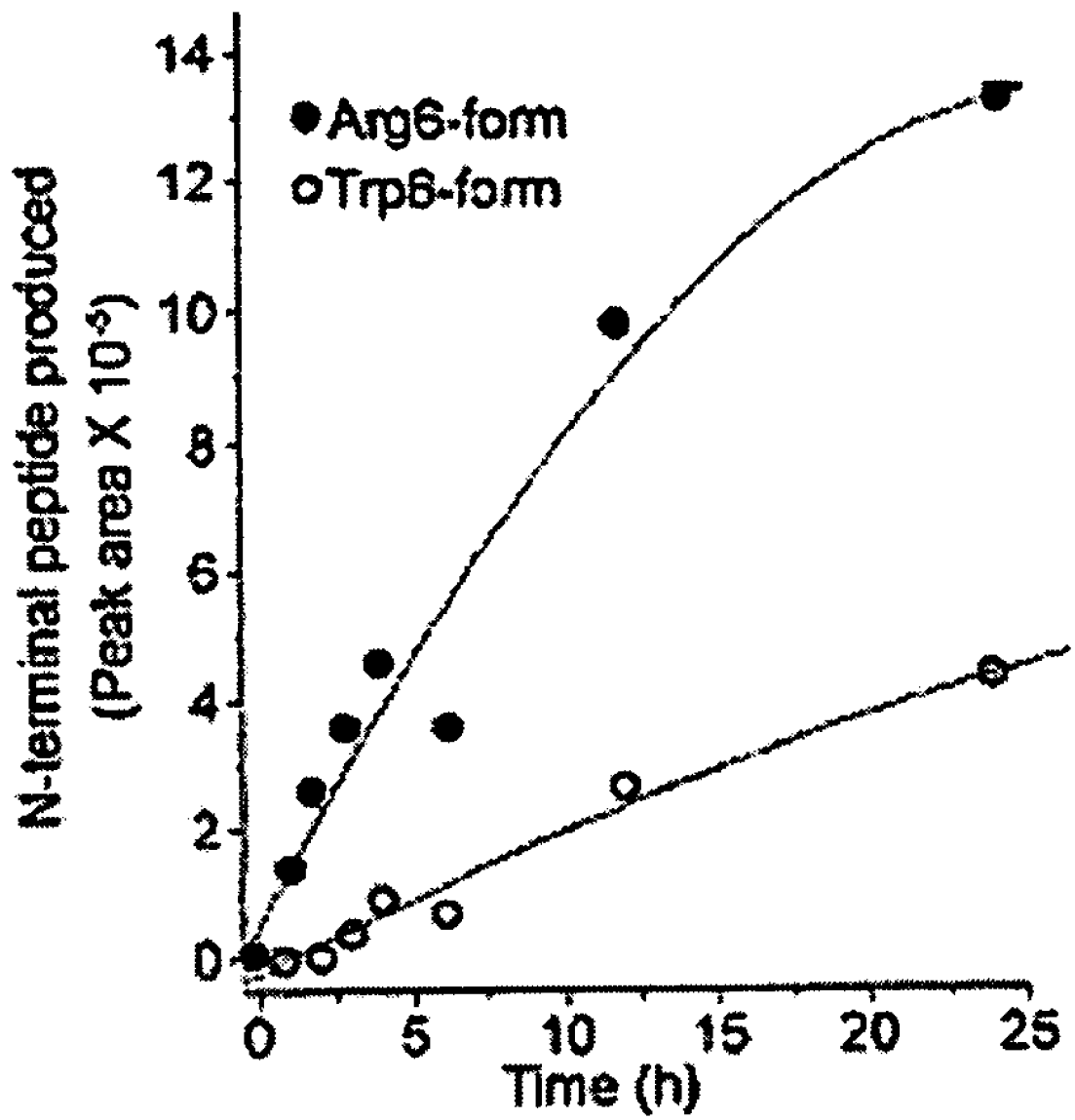
FIG. 4. Comparison of cFAP-catalyzed cleavage of Arg6- and Trp6-forms of $\alpha_2$AP$_{pro}$. Reaction mixtures containing equal amounts (each 40 µg) of $\alpha_2$AP$_{pro}$(ARG6) and $\alpha_2$AP$_{pro}$ (TRP6) were digested by partially purified cFAP. At selected times, the digestion was stopped by decreasing the pH from 7.5 to 4.0, and aliquots were assessed by ES-MS for the quantity of the N-terminal 12-amino acid peptide produced.

In order to estimate the ratio of $\alpha_2AP_{pro}$ and $\alpha_2AP_{act}$, N-terminal sequence analyses were performed on purified $\alpha_2AP$ preparations that were isolated from different fresh-frozen plasma samples purchased from the Oklahoma Blood Institute. As noted above, results from these studies indicated the existence and predicted the frequency of an Arg6Trp polymorphism in $\alpha_2AP_{pro}$. We determined that this polymorphism would result from a single nucleotide change. Table 2 shows that the ratio of $\alpha_2AP_{act}/\alpha_2AP_{pro}$ is higher in plasma containing $\alpha_2AP_{pro}$(Arg6). While several possibilities could explain this observation, we asked whether $\alpha_2AP_{pro}$(Arg6) might be a better substrate for APCE than $\alpha_2AP_{pro}$(Trp6). Indeed by electrospray mass spectrometry analysis we found that APCE cleaved $\alpha_2AP_{pro}$(Arg6) about 8-fold faster than $\alpha_2AP_{pro}$(Trp6), as shown in FIG. 4 in which comparisons of reaction rates were based on linear regression analysis of early time points.

TABLE 2

Relationship between the ratio of $\alpha_2AP_{act}/\alpha_2AP_{pro}$ and the Arg6Trp polymorphism of $\alpha_2AP_{pro}$

| $\alpha_2AP$ preparation # | $\alpha_2AP_{act}/\alpha_2AP_{pro}$* | Amino acid at position 6 |
|---|---|---|
| 1 | 3.35 | Arg |
| 2 | 0.87 | Trp |
| 3 | 1.71 | Arg + Trp |
| 4 | 1.70 | Arg + Trp |
| 5 | 2.23 | Arg |
| 6 | 2.03 | Arg |
| 7 | 1.38 | Trp |
| 8 | 4.26 | Arg |
| 9 | 2.85 | Arg |
| 10 | 3.17 | Arg |

*N-terminal sequence analysis of $\alpha_2AP$ purified from pooled human plasma revealed two parallel sequences. One starts with Met-($\alpha_2AP_{pro}$). A second sequence starts with Asn-($\alpha_2AP_{act}$). The ratio of $\alpha_2AP_{act}/\alpha_2AP_{pro}$ was expressed as (pmol of Asn)/(pmol of Met).

To facilitate the study of differences in function of $\alpha_2AP_{pro}$ and $\alpha_2AP_{act}$, we developed an antibody based affinity chromatography method to purify $\alpha_2AP_{pro}$ from a mixture of the two $\alpha_2AP$ forms. We prepared antibodies to the amino acid sequence that is unique to $\alpha_2AP_{pro}$ (NH$_2$-Met-Glu-Pro-Leu-Gly-Arg-Gln-Leu-Thr-Ser-Gly-Pro i.e., SEQ ID NO:2). The antibodies were purified from the plasma by affinity chromatography utilizing the same peptide sequence except with the addition of a C-terminal Cys to attach the peptide to the affinity support by the SH group. These purified antibodies were linked to an affinity matrix. Upon loading the $\alpha_2AP$ mixture, the $\alpha_2AP_{pro}$ will bind to the column, while the $\alpha_2AP_{act}$ will pass through. The $\alpha_2AP_{pro}$ is then eluted with 0.1 M glycine-HCl, pH 2.5. Western blot analysis and protein sequencing confirm that the eluted material is $\alpha_2AP_{pro}$.

Three independent groups have determined the amino acid sequence of $\alpha_2AP$ based on DNA sequencing (27, 28, 29), and disagreement existed on the identity of residue six. Based on DNA sequencing, two of the groups deduced Arg for the sixth position, whereas a third group deduced Trp. This discrepancy was attributed to sequencing errors particularly since the group which had Trp in the $6^{th}$ position was using cDNA from a cancer cell line, and the question of a mutation was raised. It is important to note that there has been no information suggested or published previously in current literature about differential rates of cleavage of human $\alpha_2AP_{pro}$(Arg6) versus $\alpha_2AP_{pro}$(Trp6).

Aoki's group (8, 9) presented data that N-terminal cleavage of a precursive form of $\alpha_2AP$ ($\alpha_2AP_{pro}$ in our nomenclature) gave rise to a derivative form of $\alpha_2AP$ (termed $\alpha_2AP_{act}$ by us) that was more rapidly incorporated into fibrin. They used recombinant $\alpha_2AP_{pro}$ showing that it was crosslinked into fibrin about three time slower than native $\alpha_2AP_{act}$ isolated from plasma. This is where the state of the art stood until we found that native $\alpha_2AP_{act}$ actually became incorporated into fibrin about 13-fold faster than native $\alpha_2AP_{pro}$.

No work had previously been done on the potential significance of the polymorphism. We found that with $\alpha_2AP_{pro}$(Trp6), cleavage at Pro 12-Asn 13 occurs at about one-eighth the rate of that of $\alpha_2AP_{pro}$(Arg6), and consequently significantly less of the derivative $\alpha_2AP_{act}$ should be available for crosslinking, in which case the rate of intravascular removal of fibrin by plasmin should be increased.

Prior to our purification method, studies involving $\alpha_2AP$ utilized a mixture of $\alpha_2AP_{pro}$ and $\alpha_2AP_{act}$, or at best only $\alpha_2AP_{act}$, after allowing the plasma to incubate for extended times until the endogenous cleavage agent eventually converted the $\alpha_2AP_{pro}$ to $\alpha_2AP_{act}$. Therefore, it had not been possible to ascertain any differences in function between the two $\alpha_2AP$ forms.

The present invention contemplates in one embodiment that $\alpha_2AP_{pro}$(Trp6) correlates with decreased risk of atherosclerosis and its thrombotic complications, and/or decreased tendency to develop other diseases where the development and persistence of fibrin might be undesirable (e.g., cirrhosis, pulmonary fibrosis, arthritis, various cancers and metastases). In such instances the identification of residue #6 by genotype analysis of $\alpha_2AP_{pro}$ is important in determining risk, preventative strategies, or treatment of certain diseases such as those mentioned above.

We devised a PCR reaction, using a novel set of primers (SEQ ID NO:10 and SEQ ID NO:11), to amplify a 201 base pair section of the $\alpha_2AP$ gene encompassing the polymorphism. We genotyped 17 individuals by direct sequencing of the 201 base pair fragment.

Utility

Utilities of the present invention include, but are not limited to:
(1) prevention or reduction of atherosclerotic plaque development and progression in patients at high risk;

(2) prevention or reduction of the development of arterial or venous blood clot formation in conditions recognized as high risk for such clots, i.e. heart attack or stroke;

(3) enhanced maintenance of vessel patency by continuous administration of an inhibitor of APCE, possibly in association with simultaneous administration of low doses of plasminogen activator drugs;

(4) prevention or reduction of fibrin formation where it may cause persistent acute or chronic symptoms in association with inflammatory conditions such as all forms of arthritis, organ fibrosis, undesirable scarring, and cancer and its metastases;

(5) reduction of the risk of bleeding as a hyperfibrinolytic state is induced, given that $\alpha_2AP_{pro}$ inhibits plasmin in solution state as well as $\alpha_2AP_{act}$, when not crosslinked into fibrin;

(6) aiding in the prevention and therapy of fibrin deposits interfering with organ function as might be seen in atherothrombotic disease, such as coronary artery thrombosis, stroke, pulmonary embolism, all other forms of arterial and venous thromboses, inflammatory conditions, and cancer and its metastases;

(7) determining whether a subject has a Trp6 or Arg6 polymorphism in $\alpha_2$-antiplasmin; and (8) screening for inhibitors of antiplasmin cleaving enzyme.

Various embodiments of the invention therefore include, but are not limited to:

(1) a therapeutic method of inhibiting fibrin digestion in vivo, comprising administering to a subject an effective quantity of antiplasmin cleaving enzyme or a composition thereof comprising a pharmaceutically suitable carrier;

(2) a therapeutic method of promoting fibrin digestion in vivo, comprising administering to a subject an effective quantity of an inhibitor of antiplasmin cleaving enzyme;

(3) an inhibitor of antiplasmin cleaving enzyme, wherein the inhibitor may optionally be linked to a polymeric carrier;

(4) a monoclonal antibody raised against antiplasmin cleaving enzyme, the monoclonal antibody able to bind to a non-active-site portion of antiplasmin cleaving enzyme or specifically to the active site of antiplasmin cleaving enzyme, said active site effective in cleaving at the pro-asn linkage of $\alpha_2AP_{pro}$, and wherein the monoclonal antibody able to bind to the non-active-site portion interferes with the activity of the antiplasmin cleaving enzyme;

(5) an inhibitor of antiplasmin cleaving enzyme which is effective in binding to or blocking the $\alpha_2$-antiplasmin binding site, or $\alpha_2$-antiplasmin pro-asn cleaving site of antiplasmin cleaving enzyme;

(6) a method of enhancing fibrin digestion in vivo, comprising providing to a subject in need of clot digestion or clot prevention, simultaneously or in sequence, a quantity of plasminogen activator and an inhibitor of antiplasmin cleaving enzyme, wherein the quantity of plasminogen activator is less than the amount provided in standard therapeutic protocol absent the inhibitor of antiplasmin cleaving enzyme;

(7) a method of identifying in a subject a single nucleotide polymorphism at amino acid position 6 in $\alpha_2AP_{pro}$, wherein the single nucleotide polymorphism is arginine versus tryptophan, wherein for example the polymorphism may indicate an enhanced risk for atherosclerosis or its complications or other diseases related to fibrin deposition;

(8) a method of screening for inhibitors of APCE by providing a fluorescent resonance energy transfer peptide comprising a proline-asparagine sequence and which can be cleaved at the proline-asparagine bond via antiplasmin cleaving enzyme, providing a quantity of antiplasmin cleaving enzyme, exposing the antiplasmin cleaving enzyme to an antiplasmin cleaving enzyme inhibitor candidate to form a test mixture, combining the test mixture with the fluorescent resonance energy transfer peptide and measuring the fluorescence emission from the test mixture to determine if the antiplasmin cleaving enzyme inhibitor candidate inhibits the activity of antiplasmin cleaving enzyme, wherein the fluorescent resonance energy transfer peptide may comprise a quenching group upstream of the proline-asparagine bond and a fluorophore downstream of the proline-asparagine bond, or a quenching group downstream and a fluorophore upstream of the proline-asparagine bond, and further, the FRET peptide may comprise the sequence: arg-$x_1$-thr-ser-gly-pro-asn-gln-glu-gln-$x_2$-arg, (SEQ ID NO:9), wherein $x_1$=lys-DABCYL and $x_2$=glu-EDANS, or a sequence comprising at least one conservative substitution of the amino acids upstream or downstream of the pro-asn dipeptide portion, further the FRET peptide may comprise any effective sequence having a pro-asn linkage, or gly-pro-x linkage, wherein the x is any amino acid but preferably asn, ser, ala, phe, tyr, or his, wherein in a preferred embodiment the inhibitor comprises a sequence comprising at least 5 contiguous amino acids of residues 5 to 15 (inclusive) of $\alpha_2$AP, or analogs or conservative substitutions thereof, and preferably but not necessarily includes a pro-asn linkage and a position 10 serine residue, wherein the inhibitor may be linked to a carrier protein or polymer carrier such as PEG;

(9) the APCE protein itself, or effective fragments thereof, alone or in a pharmaceutically-acceptable carrier such as a saline solution, wherein the APCE has a molecular weight of about 180 kilodaltons in SDS-PAGE in its circulating native dimeric form and has a subunit molecular weight of about 97 kilodaltons in SDS-PAGE, comprises SEQ ID NO's 1, 4, 5, 6, 7 and 8, cleaves the peptide sequence gly-pro-x on the carboxyl side of pro (wherein x is any amino acid (but is preferably asn, ser, ala, phe, tyr, or his), cleaves the methionine amino terminal precursor of $\alpha_2$-antiplasmin at the pro 12-asn13 bond to yield a truncated $\alpha_2$-antiplasmin, and has a pH optimum at 7.5±0.2; and

(10) a DNA encoding the APCE monomeric subunit.

A therapeutically effective amount of a compound of the present invention refers to an amount which is effective in controlling, reducing, or promoting a disease response as described herein. The term "controlling" is intended to refer to all processes wherein there may be a slowing, interrupting, arresting, or stopping of the progression of the disease and does not necessarily indicate a total elimination of all disease symptoms.

The term "therapeutically effective amount" is further meant to define an amount resulting in the improvement of any parameters or clinical symptoms characteristic of the disease. The actual dose will be different for the various specific molecules, and will vary with the patient's overall condition, the seriousness of the symptoms, and counter indications.

As used herein, the term "subject" or "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease or condition involved; the degree of or involvement or the severity of the disease or condition; the response of the individual subject; the particular compound administered; the mode of administration; the bioavailability characteristic of the preparation administered; the dose regimen selected; the use of concomitant medication; and other relevant circumstances.

A therapeutically effective amount of a compound of the present invention also refers to an amount of the compound which is effective in controlling or reducing a disease or another condition described herein dependent at least in part on fibrin deposition.

A therapeutically effective amount of the compositions of the present invention will generally contain sufficient active ingredient (i.e., the APCE or inhibitor thereof) to deliver from about 0.1 µg/kg to about 100 mg/kg (weight of active ingredient/body weight of patient). Preferably, the composition will deliver at least 0.5 µg/kg to 50 mg/kg, and more preferably at least 1 µg/kg to 10 mg/kg.

Practice of the method of the present invention comprises administering to a subject a therapeutically effective amount of the active ingredient, in any suitable systemic or local formulation, in an amount effective to deliver the dosages listed above. The dosage can be administered on a one-time basis, or (for example) from one to five times per day or once or twice per week, or continuously via a venous drip, or other means, depending on the desired therapeutic effect.

As noted, preferred amounts and modes of administration are able to be determined by one skilled in the art. One skilled in the art of preparing formulations can readily select the proper form and mode of administration depending upon the particular characteristics of the compound selected, the disease state to be treated, the stage of the disease, and other relevant circumstances using formulation technology known in the art, described, for example, in *Remington's Pharmaceutical Sciences*, latest edition, Mack Publishing Co.

Pharmaceutical compositions can be manufactured utilizing techniques known in the art. Typically the therapeutically effective amount of the compound will be admixed with a pharmaceutically acceptable carrier.

The compounds or compositions of the present invention may be administered by a variety of routes, for example, orally or parenterally (i.e., subcutaneously, intravenously, intramuscularly, intraperitoneally, or intratracheally).

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bioerodible carriers, such as polylactic acid and collagen formulations. Such materials may be in the form of solid implants, sutures, sponges, wound dressings, and the like. In any event, for local use of the materials, the active ingredients usually be present in the carrier or excipient in a weight ratio of from about 1:1000 to 1:20,000, but are not limited to ratios within this range. Preparation of compositions for local use are detailed in *Remington's Pharmaceutical Sciences*, latest edition, (Mack Publishing).

Additional pharmaceutical methods may be employed to control the duration of action. Increased half-life and controlled release preparations may be achieved through the use of polymers to conjugate, complex with, or absorb the compounds described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, and the appropriate concentration of macromolecules as well as the methods of incorporation, in order to control release.

Another possible method useful in controlling the duration of action by controlled release preparations and half-life is incorporation of the glycosulfopeptide molecule or its functional derivatives into particles of a polymeric material such as polyesters, polyamides, polyamino acids, hydrogels, poly(lactic acid), ethylene vinylacetate copolymers, copolymer micelles of, for example, PEG and poly(l-aspartamide).

The half-life of the molecules described herein can be extended by their being conjugated to other molecules such as polymers using methods known in the art to form drug-polymer conjugates. For example, the molecules can be bound to molecules of inert polymers known in the art, such as a molecule of polyethylene glycol (PEG) in a method known as "pegylation". Pegylation can therefore extend the in vivo lifetime and thus therapeutic effectiveness of the molecule.

PEG molecules can be modified by functional groups, for example as shown in Harris et al., "Pegylation, A Novel Process for Modifying Phararmacokinetics", *Clin Pharmacokinet*, 2001:40(7); 539-551, and the amino terminal end of the molecule, or cysteine residue if present, or other linking amino acid therein can be linked thereto, wherein the PEG molecule can carry one or a plurality of one or more types of molecules.

By "polyethylene glycol" or "PEG" is meant a polyalkylene glycol compound or a derivative thereof, with or without coupling agents or derviatization with coupling or activating moeities (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polymer conjugates include, but are not limited to, non-polypeptide polymers, charged or neutral polymers of the following types: dextran, colominic acids or other carbohydrate based polymers, biotin deriviatives and dendrimers, for example. The term PEG is also meant to include other polymers of the class polyalkylene oxides.

The PEG can be linked to any N-terminal amino acid of the molecule described herein and/or can be linked to an amino acid residue downstream of the N-terminal amino acid, such as lysine, histidine, tryptophan, aspartic acid, glutamic acid, and cysteine, for example or other such amino acids known to those of skill in the art.

The PEG moiety attached to the protein may range in molecular weight from about 200 to 20,000 MW. Preferably the PEG moiety will be from about 1,000 to 8,000 MW, more preferably from about 3,250 to 5,000 MW, most preferably about 5,000 MW.

The actual number of PEG molecules covalently bound per molecule of the invention may vary widely depending upon the desired stability (i.e. serum half-life).

Molecules contemplated herein can be linked to PEG molecules using techniques shown, for example (but not limited to), in U.S. Pat. Nos. 4,179,337; 5,382,657; 5,972,885; 6,177,087; 6,165,509; 5,766,897; and 6,217,869; the specifications and drawings each of which are hereby expressly incorporated herein by reference.

Alternatively, it is possible to entrap the molecules in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of *Remington's Pharmaceutical Sciences*.

U.S. Pat. No. 4,789,734 describe methods for encapsulating biochemicals in liposomes and is hereby expressly incorporated by reference herein. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine*, pp. 287-341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are incorporated by reference herein.

When the composition is to be used as an injectable material, it can be formulated into a conventional injectable carrier. Suitable carriers include biocompatible and pharmaceutically acceptable phosphate buffered saline solutions, which are preferably isotonic.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the compounds of the invention may be incorporated into pharmaceutical preparations which may be used for therapeutic purposes. However, the term "pharmaceutical preparation" is intended in a broader sense herein to include preparations containing a glycosulfopeptide composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of a molecule as defined herein.

All of the assay methods listed herein are well within the ability of one of ordinary skill in the art given the teachings provided herein.

All references, patents and patent applications cited herein are hereby incorporated herein in their entirety by reference.

Changes may be made in the construction and the operation of the various components, elements and assemblies described herein or in the steps or the sequence of steps of the methods described herein without departing from the spirit and scope of the invention as defined in the following claims.

CITED REFERENCES

1. D. Collen, *Thromb. Haemost.* 82, 259 (1999).
2. U. Christensen, I. Clemmensen, *Biochem. J.* 175, 635 (1978).
3. K. N. Lee et al., *Thromb. Haemost.* 80, 637 (1998).
4. K. N. Lee, W. C. Tae, K. W. Jackson, S. H. Kwon, P. A. McKee, *Blood* 94, 164 (1999).
5. R Favier, N. Aoki, P. de Moerloose, *Br. J. Haematol.* 114, 4 (2001).
6. K. Eda et al., *Jpn. Circ. J.* 65, 834 (2001).
7. H. Matsuno et al., *Thromb. haemost.* 87, 98 (2002).
8. T. Koyama, et al., *Biochem. Biophys. Res. Commun.* 200, 417 (1994).
9. Y. Sumi, Y. Ichikawa, Y. Nakamura, O. Miura, N. Aoki, *J. Biochem.* 106, 703 (1989).
10. K. N. Lee, K. W. Jackson, P. A. McKee, *Thromb. Res.* 105, 263 (2002).

11. D. F. Cunningham, B. O'Connor, *Biochim. Biophys. Acta* 1343, 160 (1997).
12. M. J. Scanlan et al., *Proc. Natl. Acad. Sci. U.S.A.* 91, 5657 (1994).
13. L. A. Goldstein et al., *Biochim. Biophys. Acta* 1361, 11 (1997)
14. P. Jeno, T. Mini, S. Moes, E. Hintermann, and M Horst, *Anal. Biochem.* 224, 75 (1995).
15. OWL database and MASCOT search engine are available at www.matrixscience.com.
16. P. Garin-Chesa, L. J. Old, W. J. Rettig, *Proc. Natl. Acad. Sci. U.S.A.* 87, 7235 (1990).
17. G. Ghersi et al., *J. Biol. Chem.* 277, 29231 (2002).
18. J. E. Park et al., *J. Biol. Chem.* 274, 36505 (1999).
19. A. Schmidt et al., *Eur. J. Biochem.* 268, 1730 (2001).
20. S. Iwaki-Egawa, Y. Watanabe, Y. Kikuya, Y. Fujimoto, *J. Biochem.* 124, 428 (1998).
21. S. Netzel-Arnett et al., *Biochemistry* 32, 6427 (1993).
22. Y. A. Birney, B. F. O'Connor, *Protein Expression and Purification* 22, 286 (2001).
23. S. Christensen, L. Sottrup-Jensen, *FEBS Lett.* 312, 100 (1992).
24. K. Okada et al., *Thromb. Haemost.* 78, 1104 (1997).
25. A. R. Thomas, R. J. Naude, W. Oelofsen, T. Naganuma, K. Muramoto, *Comp Biochem. Physiol B.* 129, 809 (2001).
26. M. Maes, *J. Affect. Disord.* 53, 27 (1999).
27. S. Hirosawa et al., *Proc. Natl. Acad. Sci.* 85, 6836 (1988)
28. W. Holmes et al., *J. Biol. Chem.* 262, 1659 (1987)
29. M. Tone et al., *J. Biochem.* 102, 1033 (1987)

SEQUENCE LISTING

```
<160> NUMBER OF SEQ ID NOS: 11

<210> SEQ ID NO 1
<211> LENGTH: 15
<212> TYPE: PRT
<213> ORGANISM: Homo sapiens

<400> SEQUENCE: 1

Ile Val Leu Arg Pro Ser Arg Val His Asn Ser Glu Glu Asn Thr
1               5                   10                  15

<210> SEQ ID NO 2
<211> LENGTH: 12
<212> TYPE: PRT
<213> ORGANISM: Homo sapiens - Human alpha2-antiplasmin

<400> SEQUENCE: 2

Met Glu Pro Leu Gly Arg Gln Leu Thr Ser Gly Pro
1               5                   10

<210> SEQ ID NO 3
<211> LENGTH: 12
<212> TYPE: PRT
<213> ORGANISM: Homo sapiens - Human alpha2-antiplasmin

<400> SEQUENCE: 3

Asn Gln Glu Gln Val Ser Pro Leu Thr Leu Leu Lys
1               5                   10

<210> SEQ ID NO 4
<211> LENGTH: 10
<212> TYPE: PRT
<213> ORGANISM: Homo sapiens

<400> SEQUENCE: 4

Tyr Ala Leu Trp Trp Ser Pro Asn Gly Lys
1               5                   10

<210> SEQ ID NO 5
<211> LENGTH: 8
<212> TYPE: PRT
<213> ORGANISM: Homo sapiens

<400> SEQUENCE: 5

Thr Ile Asn Ile Pro Tyr Pro Lys
1               5
```

```
<210> SEQ ID NO 6
<211> LENGTH: 13
<212> TYPE: PRT
<213> ORGANISM: Homo sapiens

<400> SEQUENCE: 6

Ile Leu Glu Glu Asn Lys Glu Leu Glu Asn Ala Leu Lys
1               5                   10

<210> SEQ ID NO 7
<211> LENGTH: 10
<212> TYPE: PRT
<213> ORGANISM: Homo sapiens

<400> SEQUENCE: 7

Asn Ile Gln Leu Pro Lys Glu Glu Ile Lys
1               5                   10

<210> SEQ ID NO 8
<211> LENGTH: 9
<212> TYPE: PRT
<213> ORGANISM: Homo sapiens

<400> SEQUENCE: 8

Met Ile Leu Pro Pro Gln Phe Asp Arg
1               5

<210> SEQ ID NO 9
<211> LENGTH: 12
<212> TYPE: PRT
<213> ORGANISM: Artificial Sequence
<220> FEATURE:
<223> OTHER INFORMATION: Artificially synthesized.
<220> FEATURE:
<221> NAME/KEY: MISC_FEATURE
<222> LOCATION: (2)..(2)
<223> OTHER INFORMATION: xaa at position 2 is lysine-DABCYL
<220> FEATURE:
<221> NAME/KEY: MISC_FEATURE
<222> LOCATION: (11)..(11)
<223> OTHER INFORMATION: xaa at position 11 is glutamine-EDANS

<400> SEQUENCE: 9

Arg Xaa Thr Ser Gly Pro Asn Gln Glu Gln Xaa Arg
1               5                   10

<210> SEQ ID NO 10
<211> LENGTH: 22
<212> TYPE: DNA
<213> ORGANISM: Artificial sequence
<220> FEATURE:
<223> OTHER INFORMATION: Artificially synthesized.

<400> SEQUENCE: 10
gacctcctat cctcatccct tt                                          22

<210> SEQ ID NO 11
<211> LENGTH: 21
<212> TYPE: DNA
<213> ORGANISM: Artificial sequence
<220> FEATURE:
<223> OTHER INFORMATION: Artificially synthesized.

<400> SEQUENCE: 11
ctggttcggc ccgctagtta g                                           21
```

What is claimed is:

1. An $\alpha_2$-antiplasmin cleaving enzyme, comprising: a purified protein having a molecular weight of about 180 kDa as determined by SDS-PAGE in a dimeric form, wherein each subunit of the dimeric form has a molecular weight of about 97 kDa (SDS-PAGE), and has an N-terminal amino acid consisting of isoleucine as set forth in SEQ ID NO: 1, said protein further comprising internal sequences as set forth in SEQ ID NO:4, SEQ ID NO:5, SEQ ID NO:6, SEQ ID NO:7, and SEQ ID NO:8, and wherein the enzyme cleaves precursor $\alpha_2$-antiplasmin at the pro12-asn13 bond.

2. The $\alpha_2$-antiplasmin cleaving enzyme of claim 1 having an optimum activity at pH=7.5±0.2.

* * * * *

UNITED STATES PATENT AND TRADEMARK OFFICE
CERTIFICATE OF CORRECTION

| | | |
|---|---|---|
| PATENT NO. | : 7,309,774 B2 | |
| APPLICATION NO. | : 10/774242 | |
| DATED | : December 18, 2007 | |
| INVENTOR(S) | : Patrick A. McKee et al. | |

It is certified that error appears in the above-identified patent and that said Letters Patent is hereby corrected as shown below:

In the Sequence Listing:
Column 19/20: At the end of the page and after "ctggttcggc ccgctagtta g    21" insert the following SEQ ID NO 12 – SEQ ID NO 20:

<210> 12

<211> 20

<212> PRT

<213> Homo sapiens

<400> 12

Met Glu Pro Leu Gly Arg Gln Leu Thr Ser Gly Pro Asn Gln Glu Gln
1               5                   10                  15

Val Ser Pro Leu
            20

<210> 13

<211> 20

<212> PRT

<213> Homo sapiens

<400> 13

Asn Gln Glu Gln Val Ser Pro Leu Thr Leu Leu Lys Leu Gly Asn Gln
1               5                   10                  15

UNITED STATES PATENT AND TRADEMARK OFFICE
CERTIFICATE OF CORRECTION

PATENT NO.       : 7,309,774 B2
APPLICATION NO.  : 10/774242
DATED            : December 18, 2007
INVENTOR(S)      : Patrick A. McKee et al.

It is certified that error appears in the above-identified patent and that said Letters Patent is hereby corrected as shown below:

```
Glu Pro Gly Gly
            20

<210>  14
<211>  19
<212>  PRT
<213>  Pan troglodytes

<400>  14

Met Glu Pro Leu Gly Arg Gln Leu Thr Ser Gly Pro Asn Gln Glu Gln
1               5                   10                  15

Val Ser Pro

<210>  15
<211>  19
<212>  PRT
<213>  Pan troglodytes

<400>  15

Asn Gln Glu Gln Val Ser Pro Leu Thr Leu Leu Lys Leu Gly Asn Gln
1               5                   10                  15

Glu Pro Gly
```

UNITED STATES PATENT AND TRADEMARK OFFICE
CERTIFICATE OF CORRECTION

PATENT NO.       : 7,309,774 B2
APPLICATION NO.  : 10/774242
DATED            : December 18, 2007
INVENTOR(S)      : Patrick A. McKee et al.

It is certified that error appears in the above-identified patent and that said Letters Patent is hereby corrected as shown below:

```
<210>  16
<211>  20
<212>  PRT
<213>  Baboon

<400>  16
Met Glu Pro Leu Gly Trp Gln Leu Thr Ser Gly Pro Asn Gln Glu Arg
1               5                   10                  15

Val Pro Pro Leu
                20

<210>  17
<211>  20
<212>  PRT
<213>  Baboon

<400>  17
Asn Gln Glu Arg Val Pro Pro Leu Thr Leu Leu Lys Leu Gly Asn Gln
1               5                   10                  15

Glu Pro Gly Gly
                20
```

UNITED STATES PATENT AND TRADEMARK OFFICE
CERTIFICATE OF CORRECTION

| | |
|---|---|
| PATENT NO. | : 7,309,774 B2 |
| APPLICATION NO. | : 10/774242 |
| DATED | : December 18, 2007 |
| INVENTOR(S) | : Patrick A. McKee et al. |

It is certified that error appears in the above-identified patent and that said Letters Patent is hereby corrected as shown below:

```
<210>  18
<211>  20
<212>  PRT
<213>  Bos taurus

<400>  18

Phe Ser Pro Val Ser Thr Met Glu Pro Leu Asp Leu Gln Leu Met Asp
1               5                   10                  15

Gly Gln Ala Gln
            20

<210>  19
<211>  20
<212>  PRT
<213>  Mus musculus

<400>  19

Val Asp Leu Pro Gly Gln Gln Pro Val Ser Glu Gln Ala Gln Gln Lys
1               5                   10                  15

Leu Pro Leu Pro
            20
```

UNITED STATES PATENT AND TRADEMARK OFFICE
CERTIFICATE OF CORRECTION

PATENT NO. : 7,309,774 B2
APPLICATION NO. : 10/774242
DATED : December 18, 2007
INVENTOR(S) : Patrick A. McKee et al.

It is certified that error appears in the above-identified patent and that said Letters Patent is hereby corrected as shown below:

<210> 20

<211> 11

<212> PRT

<213> Ostrich

<400> 20

Leu Gln Val Asp Tyr Leu Val Leu Glu Val Ala
1               5                   10

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,309,774 B2 |
| APPLICATION NO. | : 10/774242 |
| DATED | : December 18, 2007 |
| INVENTOR(S) | : Patrick A. McKee et al. |

It is certified that error appears in the above-identified patent and that said Letters Patent is hereby corrected as shown below:

Column 1, line 17: After "rights in" delete "some aspects of".

Signed and Sealed this

First Day of September, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,309,774 B2 |
| APPLICATION NO. | : 10/774242 |
| DATED | : December 18, 2007 |
| INVENTOR(S) | : Patrick A. McKee et al. |

It is certified that error appears in the above-identified patent and that said Letters Patent is hereby corrected as shown below:

Column 1, lines 14-17: Delete the entirety of the paragraph and replace with -- This invention was made with government support under Grant No. HL072995 awarded by the National Institutes of Health. The government has certain rights in the invention. --

Signed and Sealed this

Ninth Day of March, 2010

David J. Kappos
*Director of the United States Patent and Trademark Office*